(12) United States Patent
Gregg, II et al.

(10) Patent No.: US 12,193,891 B2
(45) Date of Patent: Jan. 14, 2025

(54) LASER ASSISTED DENTISTRY WITH RIDGE PRESERVATION (LARiP)

(71) Applicants: Robert H. Gregg, II, Huntington Beach, CA (US); Dawn M. Gregg, Huntington Beach, CA (US)

(72) Inventors: Robert H. Gregg, II, Huntington Beach, CA (US); Dawn M. Gregg, Huntington Beach, CA (US)

( * ) Notice: Subject to any disclaimer, the term of this patent is extended or adjusted under 35 U.S.C. 154(b) by 0 days.

(21) Appl. No.: 16/930,234

(22) Filed: Jul. 15, 2020

(65) Prior Publication Data

US 2021/0015584 A1    Jan. 21, 2021

Related U.S. Application Data

(60) Provisional application No. 62/875,322, filed on Jul. 17, 2019.

(51) Int. Cl.

| | |
|---|---|
| *A61C 1/00* | (2006.01) |
| *A61C 5/40* | (2017.01) |
| *A61F 2/46* | (2006.01) |
| *A61B 17/00* | (2006.01) |
| *A61B 18/00* | (2006.01) |
| *A61B 18/22* | (2006.01) |
| *H01S 5/024* | (2006.01) |
| *H01S 5/065* | (2006.01) |

(52) U.S. Cl.
CPC .............. *A61C 1/0046* (2013.01); *A61C 5/40* (2017.02); *A61F 2/4601* (2013.01); *A61B 2017/00154* (2013.01); *A61B 2018/00702* (2013.01); *A61B 2018/00732* (2013.01); *A61B 18/22* (2013.01); *H01S 5/02423* (2013.01); *H01S 5/0657* (2013.01)

(58) Field of Classification Search
CPC ...... A61F 2/4601; A61B 18/22; A61C 1/0046
See application file for complete search history.

(56) References Cited

U.S. PATENT DOCUMENTS

| | | | |
|---|---|---|---|
| 9,597,160 B1 | 3/2017 | Gregg, II et al. | |
| 2017/0215989 A1* | 8/2017 | Gregg, II | A61C 1/0015 |

OTHER PUBLICATIONS

Sharma et al, "Periotome as an Aid to Atraumatic Extraction: A Comparative Double Blind Randomized Controlled Trial", Nov. 2014 (Year: 2014).*

Amir Sanjabi DDS, 'LARiP Laser Assisted Ridge Preservation Bone Graft after Extraction of Tooth', Youtube, Mar. 6, 2015 <https://www.youtube.com/watch?v=uPsz3BXszzg>.

* cited by examiner

*Primary Examiner* — Lynsey C Eiseman
*Assistant Examiner* — Jessica L Mullins
(74) *Attorney, Agent, or Firm* — Cotman IP law group (57) ABSTRACT

A laser-assisted ridge preservation method is performed using a free-running (FR) pulsed neodymium yttrium aluminum garnet (Nd:YAG) laser device. The method includes one or more of photothermally denaturing and vaporizing encapsulated granulomatous tissues with the laser device on all sides of a socket of an extracted tooth, and irradiating the socket with the laser device to form a thrombus. A bone graft material may be placed into the thrombus.

8 Claims, 10 Drawing Sheets

| 300 Micron Fiber Preset Procedures | 360 Micron Fiber Preset Procedures | 400 Micron Fiber Preset Procedures |
|---|---|---|
| LANAP Ablation<br>100 μsec, 180 mJ, 20 Hz | LANAP Ablation<br>100 μsec, 120 mJ, 20 Hz | LANAP Ablation<br>100 μsec, 220 mJ, 20 Hz |
| Abscess<br>150 μsec, 110 mJ, 20 Hz | LANAP Hemostasis<br>550 μsec, 180 mJ, 20 Hz | LANAP Hemostasis<br>550 μsec, 220 mJ, 20 Hz |
| Aphthous Ulcers<br>150 μsec, 100 mJ, 20 Hz | Abscess<br>150 μsec, 160 mJ, 20 Hz | Abscess<br>150 μsec, 200 mJ, 20 Hz |
| Biopsy Incisional<br>100 μsec, 30 mJ, 100 Hz | Aphthous Ulcers<br>150 μsec, 160 mJ, 20 Hz | Aphthous Ulcers<br>150 μsec, 200 mJ, 20 Hz |
| Caries Removal<br>100 μsec, 210 mJ, 10 Hz | Biopsy Incisional<br>100 μsec, 40 mJ, 100 Hz | Dentin Etch<br>100 μsec, 250 mJ, 10 Hz |
| Crown Lengthening<br>150 μsec, 40 mJ, 50 Hz | Caries Removal<br>100 μsec, 300 mJ, 10 Hz | Hemostasis<br>550 μsec, 220 mJ, 20 Hz |
| Dentin Etch<br>100 μsec, 170 mJ, 10 Hz | Crown Lengthening<br>150 μsec, 60 mJ, 50 Hz | Hygiene Curettage<br>150 μsec, 120 mJ, 20 Hz |
| Diode Setting<br>100 μsec, 30 mJ, 100 Hz | Dentin Etch<br>100 μsec, 250 mJ, 10 Hz | RCT Sterilization<br>100 μsec, 180 mJ, 15 Hz |
| Fibroma<br>100 μsec, 30 mJ, 100 Hz | Diode Setting<br>100 μsec, 40 mJ, 100 Hz | Sulcular Debridement<br>150 μsec, 180 mJ, 20 Hz |
| Frenectomy<br>100 μsec, 30 mJ, 100 Hz | Fibroma<br>100 μsec, 40 mJ, 100 Hz | |
| Gingivectomy<br>100 μsec, 120 mJ, 20 Hz | LARiP Procedure<br>650 μsec, 150 mJ, 20 Hz | |
| Hygiene Curettage<br>150 μsec, 60 mJ, 20 Hz | LARiP Photobiomod.<br>100 μsec, 150 mJ, 20 Hz | |
| RCT Sterilization<br>100 μsec, 100 mJ, 15 Hz | Hygiene Curettage<br>150 μsec, 100 mJ, 20 Hz | |
| Sulcular Debridement<br>150 μsec, 100 mJ, 20 Hz | RCT Sterilization<br>100 μsec, 150 mJ, 15Hz | |
| Tissue Recontouring<br>100 μsec, 80 mJ, 50 Hz | Sulcular Debridement<br>150 μsec, 150 mJ, 20 Hz | |
| Troughing<br>250 μsec, 120 mJ, 20 Hz | Tissue Recontouring<br>100 μsec, 110 mJ, 50 Hz | |
| | Troughing<br>250 μsec, 180 mJ, 20 Hz | |
| | | |

FIG. 8 ly laser computer and a laser head assembly according to an
LASER ASSISTED DENTISTRY WITH RIDGE PRESERVATION (LARiP)

FIELD

The present disclosure relates to laser-assisted periodontal procedures, and more particularly relates to laser-assisted procedures following tooth extraction.

BACKGROUND

In the field of dentistry, it is common to use a laser to perform dental procedures such as ablation. By using a laser to perform such functions instead of, for example, mechanical tools, it is ordinarily possible to reduce the occurrence of complications and to improve therapeutic outcomes.

SUMMARY

When a tooth is extracted, it is generally best to preserve as much of the underlying jawbone (the "alveolar bone" or "alveolar process") as possible, in order to preserve the original anatomy and provide better support for, e.g., implants or bridges. One technique for minimizing the rapid initial loss of bone following tooth extraction involves placing a bone graft in the socket.

Accordingly, there is a need for a minimally invasive surgical method for preserving the alveolar process following tooth extraction which improves therapeutic outcomes and improves healing time.

Therefore, according to one example embodiment described herein, a laser-assisted ridge preservation method is performed using a free-running (FR) pulsed neodymium yttrium aluminum garnet (Nd:YAG) laser device. The method includes photothermally denaturing and vaporizing encapsulated granulomatous tissues with the laser device on all sides of a socket of an extracted tooth, and irradiating the socket with the laser device to form a thrombus. A bone graft material is placed into the thrombus.

By virtue of this arrangement, it is ordinarily possible to reduce or minimize deterioration of the alveolar process following tooth extraction, while reducing the occurrence of complications and accelerating the healing process.

According to another example embodiment described herein, a device for performing a laser-assisted ridge preservation method includes a laser device and a controller. The controller executes process steps stored in a memory to photothermally denature and vaporize encapsulated granulomatous tissues with the laser device on all sides of a socket of an extracted tooth, and to irradiate the socket with the laser device to form a thrombus. In another embodiment, photobiomodulation is used to accelerate wound healing after placement of the graft.

According to one aspect, the tooth is extracted atraumatically along a root surface and through a periodontal ligament with a periotome or periosteotome.

According to another aspect, the irradiating is performed with output power from the FR Nd:YAG laser device within 3.00 to 4.00 Watts.

According to yet another aspect, the irradiating is performed with a pulse duration from the FR Nd:YAG laser device of 650 µs.

According to still another aspect, the irradiating is performed with a repetition rate from the FR Nd:YAG laser device of 10 to 30 Hz, typically 20 Hz.

According to yet another aspect, the irradiating is performed with total output energy from the FR Nd:YAG laser device within 100 to 200 Joules for a bicuspid tooth, and 300 to 600 Joules for a molar tooth.

According to yet another aspect, granulomatous tissue is removed. In particular, in one example, a curette or FR Nd:YAG laser can be used to remove encapsulated granulomas from the socket that are greater than 1 cm$^2$ in size.

According to one aspect, the bone graft material is a spongious bone substitute which has slow resorption by host tissues.

According to another aspect, the bone graft material is placed into the thrombus midway from the depth of the alveolar process to the crestal bone, or it can be further compressed. The graft is submerged and completely contained within the blood thrombus.

According to still another aspect, in another embodiment, photobiomodulation is used to accelerate wound healing after placement of the graft.

According to yet another aspect, after the bone graft material is placed, the bone graft material is condensed with a packer or ball burnisher.

According to still another aspect, the socket is allowed to fill with blood before the irradiating.

This brief summary has been provided so that the nature of this disclosure may be understood quickly. A more complete understanding can be obtained by reference to the following detailed description and to the attached drawings.

BRIEF DESCRIPTION OF THE DRAWINGS

FIG. 8 is a view for explaining procedure-based laser parameters according to an example embodiment.

DETAILED DESCRIPTION

Environment

Figure 1:
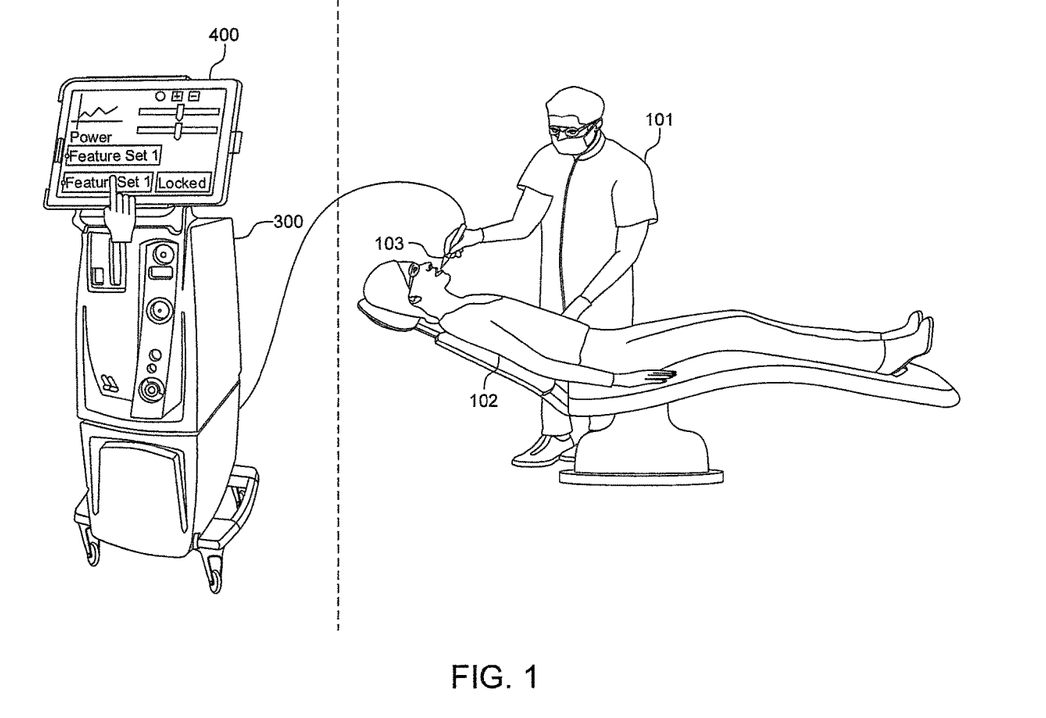
FIG. 1 is a representative view of an environment in which aspects of example embodiments may be practiced.

FIG. 1 is a representative view of an environment in which aspects of example embodiments may be practiced. In that regard, although this procedure is described with respect to a specific device (PerioLase® MVP-7™ including eGUI), it should be understood that the procedure is not limited to this device, and can be performed by other devices capable of periodontal laser dosimetry, even devices without the eGUI, such as an original MVP-7™ type laser without the eGUI.

In particular, FIG. 1 depicts an example environment in which a dentist 101 (or another clinician) inputs touch commands on a displayed eGUI of a display control subsystem 400, which in an example embodiment herein is a tablet computer 400. The commands are transmitted to a main laser computer 300 and/or a laser delivery system 103 in order to control laser delivery system 103. In the context of FIG. 1, tablet 400 is used to control the laser energy output from laser delivery system 103, which is held by dentist 101, to perform laser therapy on a patient 102. In that regard, laser delivery system 103 is also referred to as "laser 103" below for conciseness, or as "handpiece 103" below for differentiation from other hardware associated with the laser. Feedback data and other responses may be transmitted from main laser computer 300 and/or laser 103 back to tablet 400, and displayed on the eGUI.

In that regard, while a tablet is shown in FIG. 1, it should be understood that the display control subsystem may in other embodiments be implemented by numerous other types of devices to view the eGUI and communicate with main laser computer 300. More generally, a display control subsystem according to this disclosure, of which a tablet is merely an example, includes at least a display, an input for accepting user input, a processor or processing independent of that of main laser computer 300, a communication interface to laser computer 300, and storage capability. The display and the input are preferably combined into a touch-sensitive display.

Thus, it should be understood that computing equipment or devices for implementing a display control subsystem and practicing aspects of the present disclosure can be implemented in a variety of embodiments, such as a laptop, mobile phone, ultra-mobile computer, portable media player, game console, personal device assistant (PDA), netbook, or set-top box, among many others. In still another example, the device for communicating with main laser computer 300 might be attached to or communicatively coupled physically in a common housing with main laser computer 300.

For conciseness in the description that follows, the display control subsystem will hereinafter be referred to as simply a "tablet".

Main laser computer 300 contains hardware and/or software for controlling laser 103 via a wired or wireless interface. For example, main laser computer 300 may be a free-standing computing device including a hard disk and one or more processors dedicated to control of laser 103.

Laser 103 is a handheld laser for performing laser therapy including laser dentistry (e.g., ablation of bacteria in gum tissue). For example, laser 103 might correspond to a "PerioLase® MVP-7™", manufactured by Millennium Dental Technologies, Inc. In that regard, the PerioLase® MVP-7™ is a 6-Watt FR (Free-Running) Nd:YAG (Neodymium:Yttrium Aluminum Garnet) laser with features necessary to perform soft tissue procedures, and includes operator-selectable pulse durations from, e.g., 100 to 650 microseconds (µsec) to allow optimum ablation and hemostasis.

Architecture

Extensive description of architecture and other capabilities are found in U.S. application Ser. No. 14/940,126, entitled "Laser-Assisted Periodontics" and U.S. application Ser. No. 15/011,441, entitled "Laser-Assisted Periodontics", the contents of which are incorporated herein by reference.

Figure 2A:
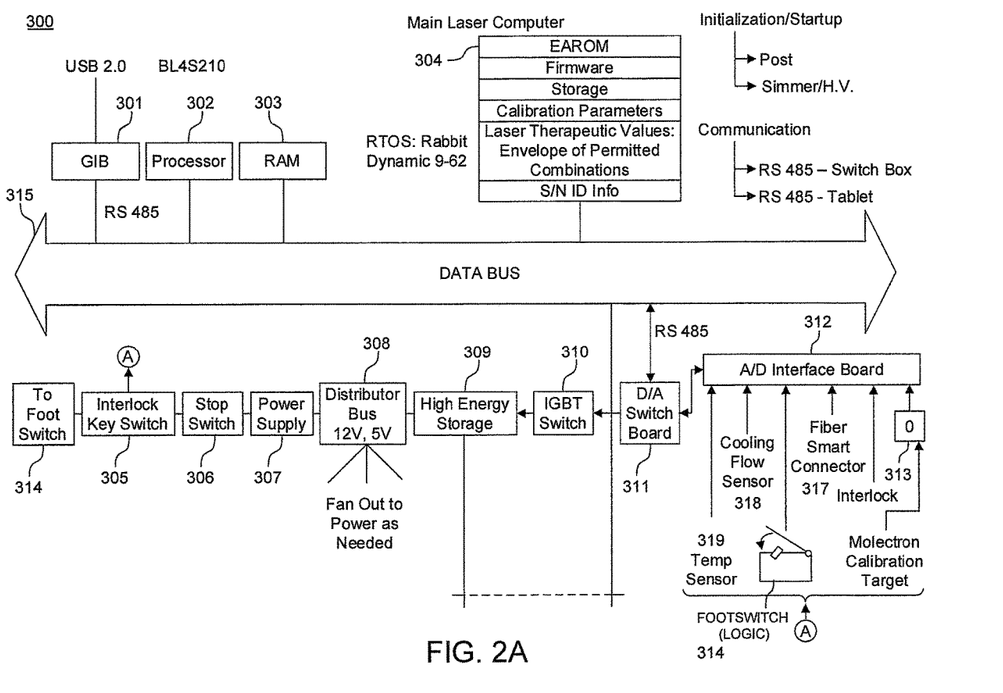
FIGS. 2A and 2B are a detailed block diagram of a main laser computer and a laser head assembly according to an example embodiment.
Figure 2B:
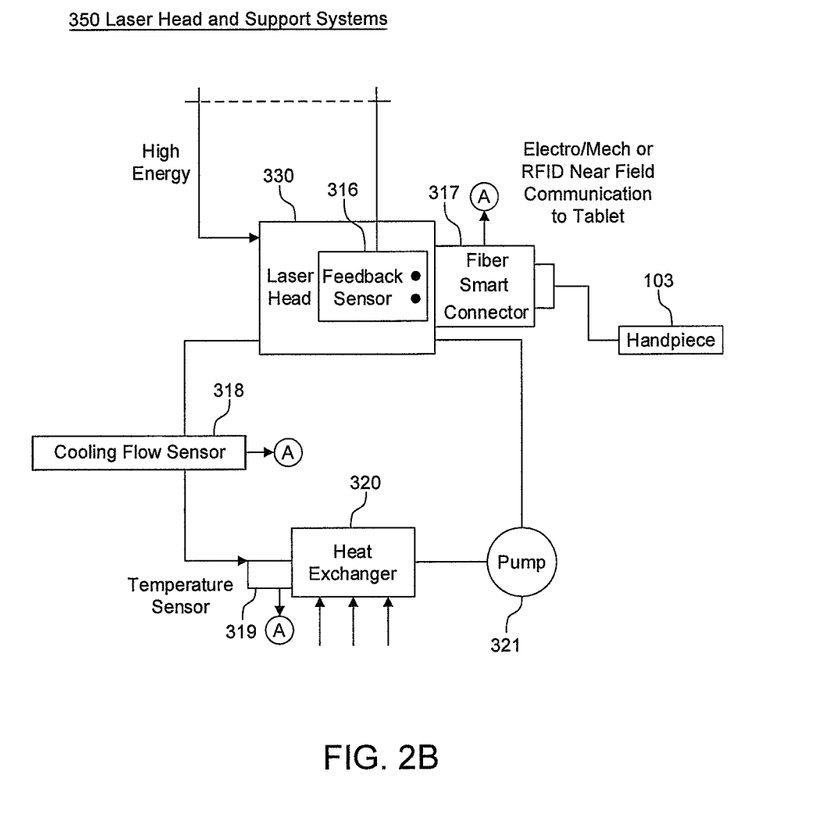

As a brief summary, FIGS. 2A and 2B are detailed block diagrams of a main laser computer 300 and a laser head assembly 350 according to an example embodiment. Main laser computer 300 interfaces to a tablet 400 depicted in more detail in FIG. 3, via an interface such as USB 2.0 as shown at GIB 301. Tablet 400 is described in greater detail below, in connection with FIG. 3.

As shown in FIG. 2A, a main laser computer 300 includes a data bus 315, a Galaxy Interface Box™ (GIB) or equivalent 301, a processor 302, RAM 303, an electronically alterable read-only memory (EAROM) or other memory functioning as a storage 304, an interlock/key switch 305, a stop switch 306, a power supply 307, a distribution bus 308, a high energy storage 309, an insulated-gate bipolar transistor (IGBT) switch 310, a digital/analog (D/A) switchboard 311, an analog/digital (A/D) interface board 312, a Molectron (calibration target) 313 and an electrical interface to a footswitch 314. Meanwhile, a laser head assembly depicted in FIG. 2B includes laser head 330 and feedback sensor 316. FIG. 2A also depicts fiber smart connector 317, including but not restricted to an electromechanical or RFID near field communication to tablet whereby the main laser computer 300 will have knowledge of the optical fiber diameter presently installed, laser delivery system 103, cooling flow sensor 318, temperature sensor 319, heat exchanger 320, and pump 321.

As a general matter, main laser computer 300 directs energy pulses having energy into laser delivery system 103. Thus, electrical energy (electrons) is converted into laser energy (photons). The laser pulse (and therefore energy supplied) may vary based on a pulse duration (in µs), an amount of instantaneous energy (in mJ), or a pulse repetition rate (in Hz), each independently selectable under software control of main laser computer 300, as described more fully below. The control to vary the pulse is important from a therapeutic perspective, as different durations, energies and the like may be beneficial under different circumstances or during different treatments. Under control of the main laser computer 300, IGBT 310 switches capacitance and inductance in order to store pulses. As far as the laser head, the use of an Nd:YAG laser is acceptable. Thus, an Nd:YAG crystal (not shown) sends out a series of pulses, directed through lenses, to a bendable optical fiber in laser delivery system 103. Fibers with different diameters can be used to, for example, specialize for certain procedures, although parameters must be recalculated to ensure that they are within acceptable limits after a fiber is switched. In order to cause the main laser computer 300 to create pulses, it is directed by a user interface on tablet 400, as described in more detail below.

Standby Mode

In standby mode, the controller sets the mains relay, capacitor board relay, simmer circuitry, and an aiming beam off. The user can select parameters at the control panel, but the footswitch will not activate the laser.

Ready Mode

When the ready button is pressed, and if no faults are present, processor 302 closes an on-board relay which powers the pump and the mains relay. The capacitor relay is still open, so the capacitor is not charged. The aiming beam is turned on after two seconds.

Firing Mode

When the footswitch is pressed in ready mode, the system enters firing mode. Processor 302 closes a second on-board relay, which provides 12V to the simmer circuitry and the capacitor relay control. Within 250 ms, the capacitor has charged and the flashlamp, a subcomponent of the laser head 330, depicted in FIG. 2B, is lit. Processor 302 then fires laser pulses at the parameters set on the control panel. Processor 302 stores the flashlamp current required for each energy level in non-volatile memory, and uses this current again when that energy is next selected. During firing, the current is continually adjusted to match the measured laser energy to the selected energy. A calibration factor, set during calibration procedures, provides the conversion. When the footswitch is released, the laser stops firing. The flashlamp remains lit for a short period, however, to allow rapid tapping of the footswitch without frequent flashlamp starts. After a period of inactivity, the system returns to standby.

In one example, when the 12V power supply comes on, processor 302 powers up and performs system tests, does a display tablet illumination (lamp) test for 2 seconds, displays the software version number, and enters the standby mode.

Thus, main laser computer 300 produces pulsed Nd:YAG laser output from a fiber-optic delivery system. Laser parameters are set by the user on a touch screen 408 (see FIG. 3) on tablet 400, and output is actuated by footswitch 314.

Processor 302 is a computer processor such as a single core or multi-core central processing unit or micro-processing unit (MPU), which is constructed to realize the functionality described below. Processor 302 might comprise multiple computer processors which are constructed to work together to realize such functionality. Processor 302 executes a computer-executable program (sometimes referred to as computer-executable instructions or computer-executable code) to perform some or all of the above-described functions. Processor 302 manages the general operation of main laser computer 300, including controls and displays, the cooling system, the laser electronics, the laser energy feedback, interlocks and sensors, and retrieving or saving data. In that regard, processor 302 executes data stored in a memory, e.g., RAM 303, in order to perform required functions. In some cases, processor 302 might comprise a single core or multi-core central processing unit (CPU) or micro-processing unit (MPU). In one example, processor 302 comprises a BL4S210 single-board computer. RAM 303 is random-access memory which allows data items to be read and written in approximately the same amount of time, regardless of the order in which data items are accessed. In addition to serving as temporary storage and working space for the operating system and applications, RAM is used in numerous other ways, which for purposes of conciseness are not described here in further detail.

In one example, communication from the tablet is via a USB interface, whereas main laser computer 300 uses an RS485 interface. To that end, GIB 301 is a Galaxy Interface Box™ for converting between USB and RS485. In particular, GIB 301 may include a USB hub so that tablet 400 can become a client and charge, i.e., a "kiosk mode" in which the hub allows fast data while also charging. In one example, GIB 301 includes a 9600 baud serial interface and is bidirectional, and charges itself from a regulated power supply via distribution bus 308.

In one brief example, upon pressure of a footswitch 314, power is directed from A/D interface board 312 to D/A switchboard 311 to IGBT switch 310 to high energy storage 309 to laser head 330. Thus, D/A switchboard 311 powers IGBT switch 310.

Data bus 315 is a communication system that transfers data between components inside main laser computer 300. In that regard, the internal structure of data bus 315 may vary.

In one example, D/A switchboard 311 provides flashlamp start and simmer functions, and converts low voltage controller signals to isolated IGBT signals. To start the flashlamp, 12V is applied to the input of a DC-to-DC converter, which applies a voltage (e.g., 1100 V) across the flashlamp. At the same time, 300 V pulses are applied to the trigger transformer primary, generating 15 kV pulses to start the flashlamp. Once the flashlamp is lit, simmer current is drawn from the pulse capacitor, and is ballasted by a bank of external simmer resistors. The flashlamp pulse current is set by a serial signal from processor 302, which controls the output of a serial digital-to-analog converter (DAC). The actual flashlamp current is monitored by a shunt resistor, and compared to the DAC output. Switching circuits modulate the IGBT 310 to set the current. The pulse width is set by a gating signal from the processor 302, which does not pass through the interface board.

In one example embodiment, laser head assembly 350 contains the pump chamber with flashlamp, Nd:YAG rod, and trigger transformer; laser cavity optics, an energy monitor, a fiber lens cell, and a diode laser aiming beam. All are supported by an aluminum and graphite/epoxy resonator structure. The flashlamp output is absorbed by the Nd ions in the YAG rod, and provides the gain which supports laser oscillation. The laser pulse shape closely matches the flashlamp electrical pulse, except for some smoothing caused by the fluorescent lifetime of the gain medium. The energy monitor contains a beam sampler, which splits off 4% of the output beam. This sampled beam is spatially integrated by a pair of opal diffusers, then converted to electrical current by a reverse-biased germanium PIN photodiode. Circuitry on the energy monitor board converts this current into a stream of digital pulses, which are counted by the controller. After subtraction of a background count, the total number of pulses is proportional to the laser energy.

High energy storage 309 is a high-energy power supply, i.e., is a storage device configured to store a relatively large amount of energy, and is switched by IGBT switch 310. The amount of energy supplied may be dependent on a switchable mode and/or input via independently selectable parameters, e.g., duration (in us), an amount of instantaneous energy (in mJ), or a pulse repetition rate (in Hz). The switch between the modes/parameters above (e.g., between different modes corresponding to different amounts of energy or between different laser parameters such as duration and instantaneous energy) may be digital. In one example, energy for the laser flashlamp is stored in a pulse capacitor. The capacitor is charged to 600 V through a step-up toroidal transformer powered from the mains relay, and a bridge rectifier on the capacitor board. The capacitor board also contains a high-voltage solid-state relay, which controls the charge timing and regulates the voltage.

Molectron 313 is a hardware power meter which acts as a calibration target. In particular, a user can aim the laser at the window of Molectron 313, and see if the laser is performing as requested. For example, Molectron 313 measures the output power, and verifies whether the average power requested or expected from a set of parameters is what is actually being output by the laser. To that end, Molectron 313 is connected to A/D interface board 312, which routes the measured power/information back to the main laser computer 300, specifically processor 302. Firmware in Molectron 313 may support such a calibration mode and provide feedback to the user via an eGUI on the tablet. Calibration in Molectron 313 works in tandem with feedback sensor 316 in laser head assembly 350, which detects the flow of energy through the laser head. In one example, ordered pairs/sets of parameters may be stored as calibration factors/best fits for an input value, e.g., average power.

A/D interface board 312 collects and converts (if necessary) various analog values, and transmits information corresponding thereto to processor 302. For example, as shown in FIG. 2A, A/D interface board collects data from Molectron 313, cooling flow sensor 318, temperature sensor 319, fiber smart connector 317, interlock/key switch 305, and footswitch 314. Accordingly, A/D interface board 312 measures, e.g., power, cooling and other housekeeping data, and processor 302 can inquire with A/D interface board 312 (or A/D interface board 312 may push information thereto) in order to verify that the laser is performing within specifications.

Thus, A/D interface board 312 monitors and receives analog or digital signals from various parts of the main laser computer 300 and laser head assembly 350, converts the information to digital data, and forwards the digital data on for processing (e.g., to processor 302). In one example embodiment, the only digital communication between the system and A/D interface board 312 is via the D/A switchboard 311. Put another way, A/D interface board 312 is responsible for taking in analog inputs and converting them to digital information, but the D/A switchboard 311 acts as a messenger to forward that information from A/D interface board 312 to other components in main laser computer 300. Accordingly, in such an example embodiment, A/D interface board 312 does not directly communicate with other components such as processor 302.

Footswitch 314 is a physical pedal or other foot-actuated hardware which sends a signal upon being pressed, such as a signal indicating to fire the laser. Of course, the physical element for activating the laser is not limited to a footswitch, and other hardware elements and control are possible. Footswitch 314 is connected to A/D interface board 312 in order to transmit signals to the main laser computer 300.

Interlock key switch 305 is the physical connection to an external main power supply (e.g., via a plug), and is connected to stop switch 306. Together, these elements perform line filtering, as well as act as a two-step fail-safe for providing or cutting power, and are connected to power supply 307.

Power supply 307 is a regulated power supply, and acts as an embedded circuit to input unregulated energy into a stable power supply, e.g., a stable voltage or current within set limits. In one example, AC mains enters at the back panel, and is fused and filtered. The front panel key switch controls AC input to the 12V power supply, which powers the controller and all low voltage components.

Distribution bus 308 fans power out to elements of main laser computer 300 as needed. To that end, distribution bus includes a 5V output and a 12V output, among others as necessary. For example, parallel circuits allow distribution bus 308 to transmit power to high energy storage 309.

IGBT switch ("IGBT") 310 is a solid-state switch which acts as an amplifier of signals from D/A switchboard 311. In one example, IGBT 310 is essentially a large transistor, acting as an amplifier. D/A switchboard 311 acts together with the IGBT to control high energy storage 309 to drive the laser head assembly 350. The laser may need to "simmer" prior to usage, in which a certain lower amount of power is used to get the laser ready for firing. In one example, the shape of the current pulse is controlled by the IGBT 310 and a smoothing inductor. The IGBT 310 allows control of both the amplitude and width of the pulse.

EAROM 304 for main laser computer 300 stores firmware programs for controlling the operation of main laser computer 300, as well as data corresponding thereto. In one example embodiment, a software architecture stored in EAROM 304 includes a real-time operating system (RTOS) based on dynamic C programming (e.g., version 9.62), a monitoring module, an initialization/startup module (such as for controlling a "simmer" mode for warming up the laser), a firing module for controlling firing of the laser, and a communication module for performing, e.g., RS285 communication to D/A switchboard 311 (for internal communications) and to GIB 301 (for external communications). EAROM 304 also stores calibration factors and calibration values in a persistent manner, and can return appropriate signals for the IGBT 310 and A/D interface board 312 in accordance with requested signal parameters. EAROM 304 may also store permissible values or a "permissible therapeutic window" which includes combinations of laser parameter values. Examples can be seen in U.S. Publication No. 2003/0108078. EAROM 304 may also store other housekeeping information, such as a serial number of the laser.

In the laser head assembly 350, a cooling system includes cooling flow sensor 318, temperature sensor 319, and heat exchanger 320. Cooling includes both primary and secondary systems. The primary system may include distilled water conduction (flow) through the laser head 330, and a secondary system may use forced convection (a fan). Cooling flow sensor 318 issues an analog signal indicating whether the amount of flow through the laser head is acceptable or not, and interfaces to A/D interface board 312. Heat exchanger 320 is a forced convection heat exchange, e.g., a small control loop for the fan which monitors temperature through temperature sensor 319, transfers heat as necessary, and reports temperature to A/D interface board 312.

In one example, the cooling system consists of a 12V brushless DC pump, a heat exchanger, a 12V brushless DC temperature-sensing fan, a flow switch, a thermistor sensor, and connecting corrugated Teflon tubing. The coolant is approximately 400 ml of de-ionized or distilled water. The fan is powered directly from the 12V supply, but includes temperature sensing circuits to monitor the coolant temperature. If the coolant reaches 40° C., the fan speed increases gradually. The controller board contains a relay which drives the pump 321. The controller also monitors the coolant temperature via the thermistor.

Fiber smart connector 317 is connected to laser head 330, laser delivery system 103 and A/D interface board 312, and acts to transfer information such as analog feedback to A/D interface board 312 (which is then converted to digital information for processor 302), as well as to detect certain conditions on its own. For example, fiber smart connector 317 can detect the fiber diameter in laser delivery system 103, and then relay this information to main laser computer 300 or tablet 400. In one example, parameters must be recalculated to ensure that they are within acceptable limits after a fiber is switched. Error codes may be transmitted from smart connector in accordance with a mismatch between fiber and parameters, or in accordance with any other conditions that are out of specification.

In one aspect, analog feedback from fiber smart connector 317 to A/D interface board 312 may be sent via near-field communication (NFC), radio-frequency identification (RFID) transmissions, and the like. For example, analog feedback may be sent to confirm the laser fiber diameter if the user has changed the fiber, but wants to keep the same power density, as well as to confirm that the laser parameters meet safety requirements.

Feedback sensor 316 detects the flow of energy through laser head 330, and tells processor 302 the status of the laser, including parameters such as, e.g., average power. Feedback sensor may also be configured to transmit an error message to stop the laser, as a fail-safe for when the laser appears to be operating incorrectly.

Figure 3:
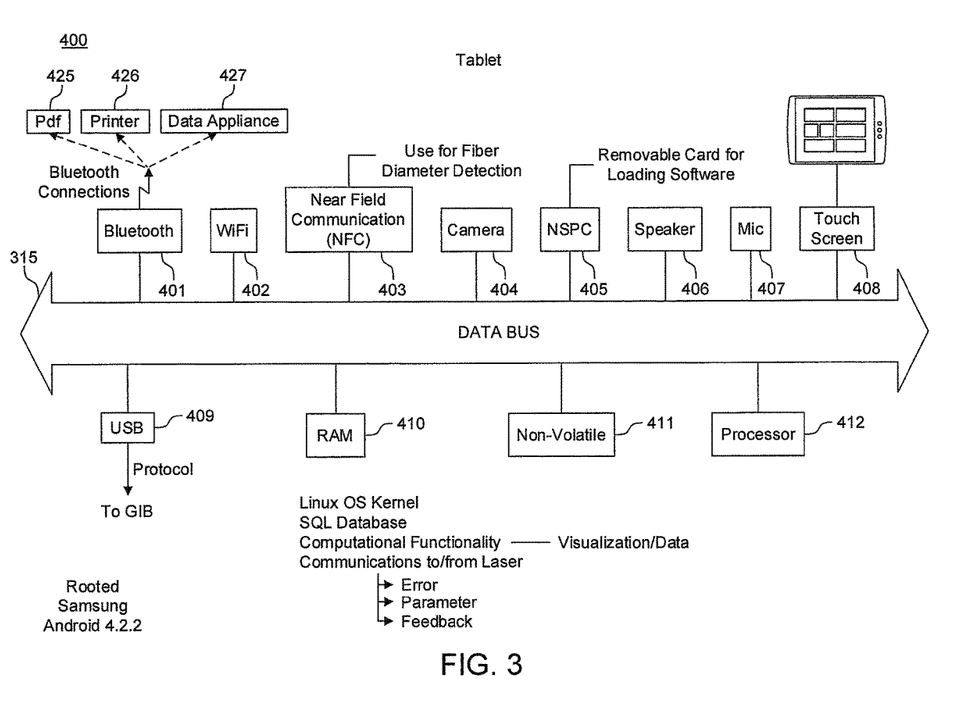
FIG. 3 is a detailed block diagram of a display control subsystem in the form of a tablet computer according to an example embodiment.

FIG. 3 is a detailed block diagram of a tablet 400 according to an example embodiment. As noted above, tablet 400 interfaces to main laser computer 300 via an interface such as USB 409, which communicates with the GIB 301 of main laser computer 300 shown in FIG. 2A.

As shown in FIG. 3, tablet 400 includes bus 413, Bluetooth unit 401 connecting to pdf element 425, printer 426 and data appliance 427, WiFi unit 402, near-field communication (NFC) unit 403, camera 404, nonparametric statistical process control (NSPC) unit 405, speaker 406, microphone 407, touch screen 408, USB 409, RAM 410, non-volatile memory 411 and processor 412.

Generally, tablet 400 may run on a Linux/Unix-based Operating System (OS). For example, tablet 400 may be an Android™ tablet or equivalent running OS version 4.2.2. Of course, numerous other variations on hardware and software are possible.

According to one embodiment, default safeguards are modified or eliminated to allow for direct calls to the OS (e.g., from main laser computer 300), thereby allowing the tablet 400 to be used as an effective control system. In another example, variants of Linux allowing such calls may be used.

The main functionality of tablet 400 covers a variety of aspects. In one aspect, functionality is computational, such as receiving calls to a relational database in non-volatile memory 411, e.g., recording data for a particular patient or user, including a location in the mouth and observations related thereto, as well as computing a new set of laser parameters in accordance with a user request on touch screen 408 to change a different parameter, and forwarding such parameters to main laser computer 300 for verification. In another aspect, tablet 400 functions as a communication medium between a user and main laser computer 300, and performs functions such as transmitting data to and from main laser computer 300, including commands, feedback, error codes, and input laser parameters.

Insofar as the eGUI is concerned, it should be understood that various display and control arrangements are possible. For example, numerous aspects of the eGUI can be found in U.S. application Ser. No. 15/011,441, entitled "Laser-Assisted Periodontics", the contents of which are incorporated by reference herein. In addition, numerous aspects of different eGUI screens and controls will be described more fully below with respect to FIGS. 6 and 7.

Nevertheless, for purposes of clarity, an example embodiment will be described which includes four main "control surfaces" on the displayed eGUI which can be switched between using, e.g., a "swipe" on touch screen 408.

First, a "home screen" provides main command and control functionality, including control of patient management and of main functionality of the laser. For example, the home screen allows a user to view information concerning a patient selected from a patient management surface (described below), to select and vary clinical laser parameters, to select a quadrant of the mouth, tooth or tooth group for treatment, and the like. In addition, the home screen allows for monitoring and control of the laser itself. For example, the home screen may display "standby", "ready" or "FIRE" as the status of the laser, in accordance with the operation of the laser in response to a press of footswitch 314.

In one example aspect, when the footswitch 314 is actuated, information including the patient, tooth, etc. selected or displayed on the tablet eGUI is saved to non-volatile memory 411 in the tablet, along with a running total of energy, pulses, parameters, dosimetry and the like for the period in which the footswitch is depressed, and an editable name for the current treatment period, e.g., "Remove Tissue—Form Thrombus".

In one example embodiment, the recorded data may be used to recommend new laser parameters. For example, treatment feedback may be fed to a data apparatus, and may be used to calculate new recommended laser parameters for the current patient and procedure.

In another example, a manual power measurement mode may allow for laser data to be saved without being tied to a patient. For example, if a threshold energy is reached, recording may stop and measurement of power may begin, even if the user is not currently using Molectron 313.

Second, a "patient management screen" allows for access and display of information from a database of up to thousands of patients or more, as well as providing manipulation of such information, such as adding, deleting, or selecting a patient.

In one example, information about a patient is displayed (e.g., name, ID number, dental history), along with, e.g., dental records or links thereto. Thus, the patient management screen can integrate electronic dental records, as required in some instances by Federal law. For example, the patient management screen can provide digital reports in a HIPAA-compliant manner, which can be readily integrated with patient data files. In that regard, additional security measures may prevent unauthorized persons from offloading the information gathered.

Third, a "procedures control surface" allows for selection and control of laser procedures, and may include, for example, a table with preset laser parameters (e.g., in sets or "triplets" comprising three parameters) for sample procedures.

In one aspect, the procedures control surface is used to provide training procedures for users such as a dentist and clinician. For example, a user may log into the home screen, after which the eGUI depicts information about the currently logged-in dentist or other user, such as name, ID number, and, for example, an indication of training or certification and what corresponding service modes are available. In that regard, the term "dentist" is used here for purposes of conciseness, but it should be understood that "clinician" and the like could also be used. In addition, service modes may allow, e.g., operation of the laser at fixed current and pulse width, while monitoring the internal energy monitor, and changing a calibration factor, to match the laser output to an external power meter testing of the capacitor charge, whereas another service mode might allow testing of flash-lamp start and simmer circuits, setting of the initial flash-lamp current, and display of the coolant temperature. Yet another service mode might restore default parameters, display energy monitor counts, or the like.

The procedures control surface may provide advanced features and capabilities for control of laser as user training and certification permit. Thus, in one example, procedures control surface allows for training, in which additional features or options are made available only after the user has performed a training course. For example, while a control box may be shown for selection of one feature set, another feature set may be displayed with a lock icon indicating that the feature set is currently unavailable (e.g., because of insufficient training). The procedures control surface may also display icons indicating levels of training which have been performed. Additional aspects regarding clinician training and general laser dentistry procedures (in the context of the LAPIP™ protocol) can be found in U.S. application Ser. No. 14/940,126, entitled "Laser-Assisted Periodontics", the contents of which are incorporated by reference herein.

In one embodiment, a database (e.g., SQL) or table stores a correspondence between each user and authorized procedures and corresponding laser parameters. For example, a value of 0, 1, or 2 may be assigned for a user for certain procedures, with 0 indicating that the user can see the procedure but not use it, a 1 indicating that the user has access to that procedure/parameters and can use them, and a 2 indicating that the user can see, use, and even overwrite the parameters for a given procedure. In that regard, the corresponding eGUI may be more simple than the stored table values. In addition, controls such as overriding parameters for a procedure may require transfer to the home screen (with or without a corresponding warning), since the home screen governs more basic controls.

In a real-world example, controls on the procedures control surface can be integrated with a training program from, e.g., the Institute for Advanced Laser Dentistry (IALD). The IALD is an American Dental Association Continuing Education Recognition Program (ADA CERP®) Recognized Provider and an Academy of General Dentistry Approved PACE Program Provider that administers a CE training program that includes a standard proficiency course along with four days of hands-on, live-patient clinical instruction to ensure success by the practitioners.

Thus, features in the procedures control surface can be synthesized from impactful portions of the IALD training continuum. Accordingly, the procedures control surface can be designed to reflect the training, rather than altering training to fit a device design.

In one example, the procedures control surface is configured so that the clinician who is in the midst of completing his/her training will have access to only the features of the laser for the LARiP™, LANAP® and LAPIP™ protocols that they have learned at that point in training, commensurate with their level of clinical proficiency as certified by the IALD. In addition, these clinicians will also learn additional value-added procedures (VAPs™), based on their level of training. In one example, a unique password is issued to each dentist at the completion of each level of training, which reveals the features that are appropriate. For example, in the context of IALD certifications, clinicians might receive new passwords after they complete Laser BootCamp®, after they complete Evolution 4, and after they complete Evolution 5. With such control of access to laser control, the IALD can give LARiP™ clinicians-in-training the access to only what they have learned. This will increase safety of LARiP™ patients, and will guide the clinicians toward techniques and therapeutic settings, encouraging them to use only the techniques that they have mastered up to that point.

In addition to the above, the procedures screen may also display a light dose chart, showing an amount of laser dosimetry over time, as well as a line indicating the maximum dosage allowed for that tissue/procedure. For example, the procedures screen may, using information from the patient records, determine a disease being treated and a dosage administered thus far, and display a "max" line on a graph, with a dosage line which increases in real time toward the maximum as further laser dosage is applied. This screen is described more fully below with respect to FIG. 7.

An "Admin" maintenance/settings screen may allow for general housekeeping and maintenance control, such as setting a time zone or date, adjusting display settings such as selecting between a simplified and more complex display, control icons, and the like.

In one example, the tablet eGUI may show which combinations of laser parameters (e.g., duration (in µs), an amount of instantaneous energy (in mJ), or a pulse repetition rate (in Hz) as discussed above) are allowed and/or within safe limits. Put another way, the tablet eGUI may use rules to keep parameters within specified therapeutic "windows", and prevent control of parameter values outside such windows. For example, a user or administrator might be able to unlock a locked parameter (e.g., instantaneous energy), but the system may force the other two parameters to safe boundaries in accordance with the newly selected instantaneous energy, and display information as such to the user.

Such control may be enforced from main laser computer 300, and then transmitted to the tablet 400 to display on the eGUI. In another example, having received a recalculation of a locked (or unlocked) parameter, tablet 400 may perform a recalculation of other parameters at its end, and then transmit the new parameters to main laser computer 300 for validation or refusal (e.g., as indicated by an error message, grayed-out parameter values, etc.). Generally, main laser computer 300 will not send an illogical choice of parameters to the laser, whereas the tablet will not allow selection of an illogical combination at the user end on the display. The tablet 400 may store default combinations of parameters.

Turning to the hardware of tablet 400, in one example, RAM 410 is random-access memory which allows data items to be read and written in approximately the same amount of time, regardless of the order in which data items are accessed. In addition to serving as temporary storage and working space for the operating system and applications, RAM is used in numerous other ways, which for purposes of conciseness are not described here in further detail.

Bluetooth 401, WiFi 402 and NFC 403 variously act as wireless network units for wirelessly interfacing with main laser computer 300 or other devices, whereas USB 409 acts as a physical connection to other devices. Bluetooth 401 is hardware/software for exchanging data over short distances (using short-wavelength UHF radio waves in the Industrial, Scientific and Medical (ISM) bands from 2.4 to 2.485 GHz) from fixed and mobile devices, WiFi 402 is hardware/software for local area wireless communications, and NFC 403 is hardware/software for NFC-protocol-based radio communication with nearby devices or elements.

In some examples, these units interface with a data appliance 427, shown in FIG. 3. Data appliance 427 is, e.g., a physically and electronically secure data server with hardwired digital electronic interfaces and wireless digital electronic interfaces. Data appliance 427 may act as a more secure storage for data such as patient records, including HIPAA reports. In some cases, the tablet 400 may first transmit such data to data appliance 427 using Bluetooth, which then offloads the data to another computer such as a PC (not shown). Such a transfer can also be two-way, in that information such as recommendations can be transmitted back to the tablet, with treatment progress and recommendations re-synchronized again with the PC after new treatment, etc. In some cases, WiFi may be used to transmit data from the tablet if, under the circumstances, it is more secure (or HIPAA compliant).

Camera 404 is an optical instrument for recording images, which may be stored locally, transmitted to another location, or both. The images may be individual still photographs or sequences of images constituting videos or movies.

NSPC 405 is hardware/software for monitoring and controlling processes in tablet 400 to ensure that it operates at or near its full potential. Speaker 406 is an electromechanical element which produces sound. Microphone ("Mic") 407 is an acoustic-to-electric transducer or sensor that converts sound into an electrical signal.

Touch screen 408 is a hardware/software input device normally layered on the top of an electronic visual display, by which user can give input or control the information processing system through simple or multi-touch gestures by touching the screen with a special stylus/pen and/or one or more fingers. As described above, touch screen 408 displays several eGUIs and controls, along with various data.

USB 409 is a connector for communicating via the Universal Serial Bus protocol, and in particular, is used to communicate from tablet 400 to main laser computer 300 via GIB 301.

Non-volatile memory 411 is computer memory that can retrieve stored information even after having been power-cycled. Examples of non-volatile memory include read-only memory, flash memory, ferroelectric RAM (F-RAM), most types of magnetic computer storage devices (e.g. hard disks, floppy disks, and magnetic tape), and optical discs.

Processor 412 is a computer processor such as a single core or multi-core central processing unit or micro-processing unit (MPU), which is constructed to realize the functionality described below. Processor 412 might comprise multiple computer processors which are constructed to work together to realize such functionality. Processor 412 executes a computer-executable program (sometimes referred to as computer-executable instructions or computer-executable code) to perform some or all of the above-described functions.

Laser-Assisted Ridge Preservation Procedure (LARiP™ Protocol)

Figure 4A:
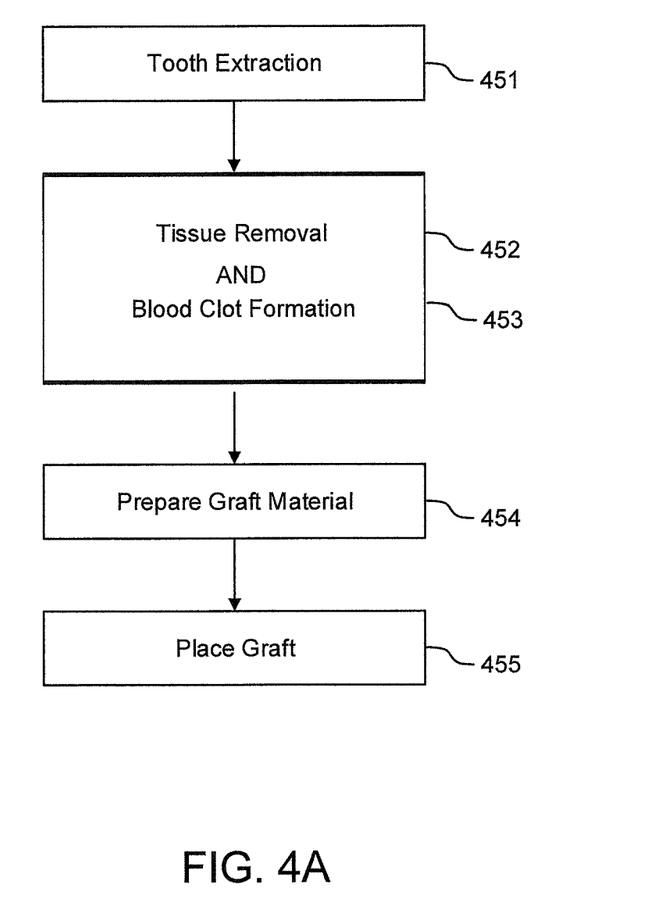
FIGS. 4a and 4b are flow diagrams for explaining a laser-assisted ridge preservation procedure (LARiP™ Protocol) according to example embodiments.
Figure 4B:
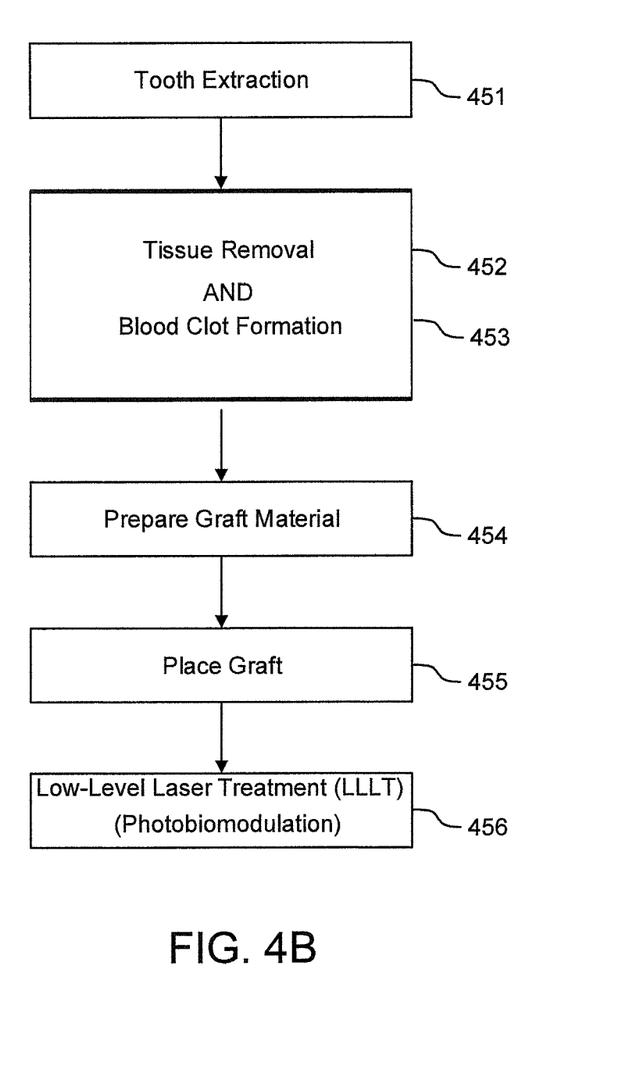

FIG. 4 is a flow diagram for explaining a laser-assisted ridge preservation procedure (LARiP™ Protocol) according to an example embodiment.

Briefly, as shown in FIG. 4, a laser-assisted ridge preservation procedure is performed using a free-running (FR) pulsed neodymium yttrium aluminum garnet (Nd:YAG) laser device. The procedure includes photothermally denaturing and vaporizing encapsulated granulomatous tissues with the laser device on all sides of a socket of an extracted tooth, and irradiating the socket with the laser device to form a thrombus. A bone graft material is placed into the thrombus In step 451, a tooth is atraumatically extracted. For example, the tooth is separated from the surrounding bone by slicing along the root surface and through the periodontal ligament with a sharp periotome or periosteotome.

In step 452, tissue is removed. In particular, in one example, a curette or PerioLase Nd:YAG laser can be used to remove encapsulated granulomas from the socket that are greater than 1 cm². In that regard, the procedure used to remove tissue may be similar to that described in the aforementioned U.S. patent application Ser. No. 14/940,126 or the aforementioned U.S. patent application Ser. No. 15/011,441.

In step 453, the extraction site is allowed to fill with blood, and then irradiation is performed in the socket with the PerioLase Nd:YAG laser 103 to form a stable thrombus. Mechanical instrumentation, in one example, a curette, can be used to encourage and initiate blood to fill the extraction site.

In one example, the parameters for the irradiation may include, e.g., 3 to 4 Watts (100 to 300 mJ, 10 to 30 Hz), or more specifically, 3.00 to 3.60 Watts. Typical Pulse duration is 650 µs, and the Repetition Rate is 20 Hz. The total energy delivered can range between 100 to 200 Joules for a bicuspid to 300 to 600 Joules for a molar. Clinical conditions guide the selection of parameters used, and the surgical endpoint determines the total Joules delivered. As a visual end point for the clinician, the blood will turn from red to a rust or brown color, and/or the blood will foam or bubble.

In step 454, bone graft material is prepared. In preparation of the bone graph material, a spongious bone substitute which has slow resorption by host tissues, e.g., Geistlich® Bio-Oss Collagen®, can be used. In that regard, fast resorption tends to lose the graft material and produce a "dry socket". In one example, a graft may be cut from Bio-Oss Collagen® cut to a piece that fills the socket, and condensed with a packer or ball burnisher.

In step 455, the bone graft is placed. This process is described more fully below with respect to FIG. 5.

In another embodiment, in step 456, photobiomodulation is performed to accelerate the wound healing. Typical photobiomodulation parameters include a pulse duration of 100 µs, 3.0 to 6.0 Watts (150 to 300 mJ, 20 Hz), 1500 to 3000 Watts peak power, number of Joules varies.

Figure 5:
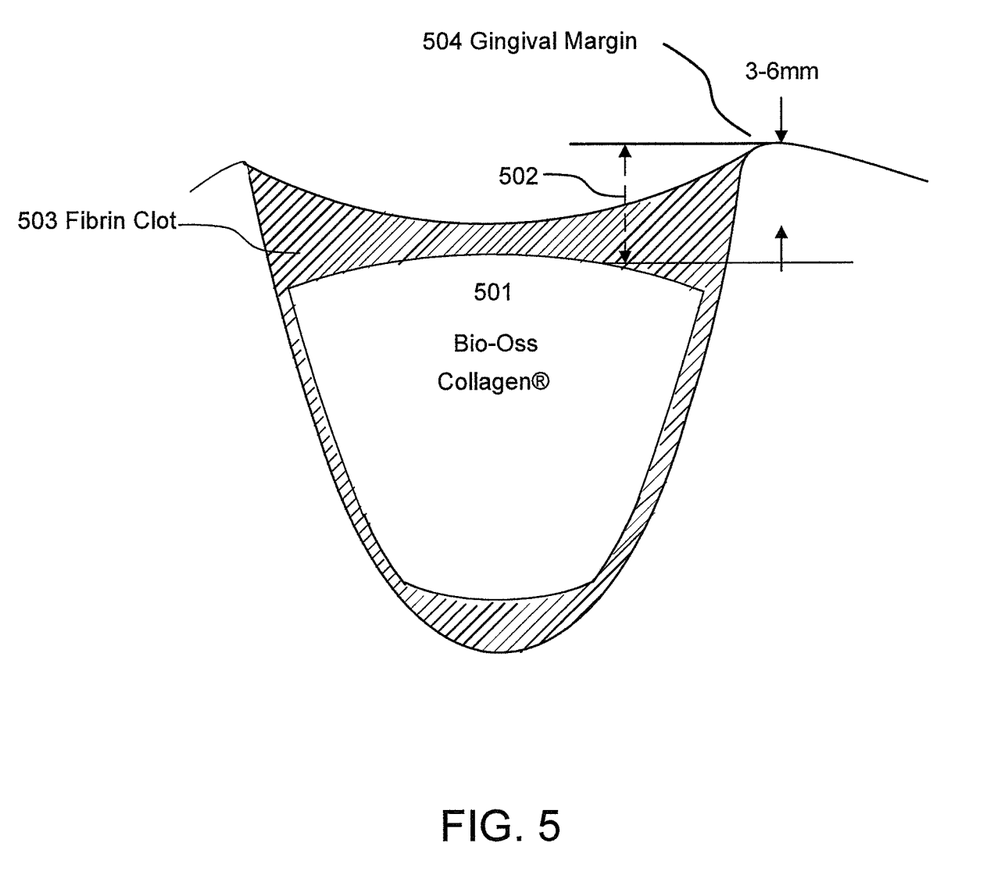
FIG. 5 is a view for explaining bone graft preparation according to an example embodiment.

FIG. 5 is a view for explaining bone graft placement according to an example embodiment.

As shown in FIG. 5, graft material 501 is placed into a thrombus 503 midway in the alveolus 505 from the depth of the alveolar process to the crestal bone 504, or it can be further compressed. The graft is submerged 502 and completely contained within the blood thrombus. The graft material is condensed with a packer or ball burnisher. The bone graft material ("Bio-Oss Collagen®") soaks up the blood, disperses and expands.

Graphical User Interface

Figure 6:
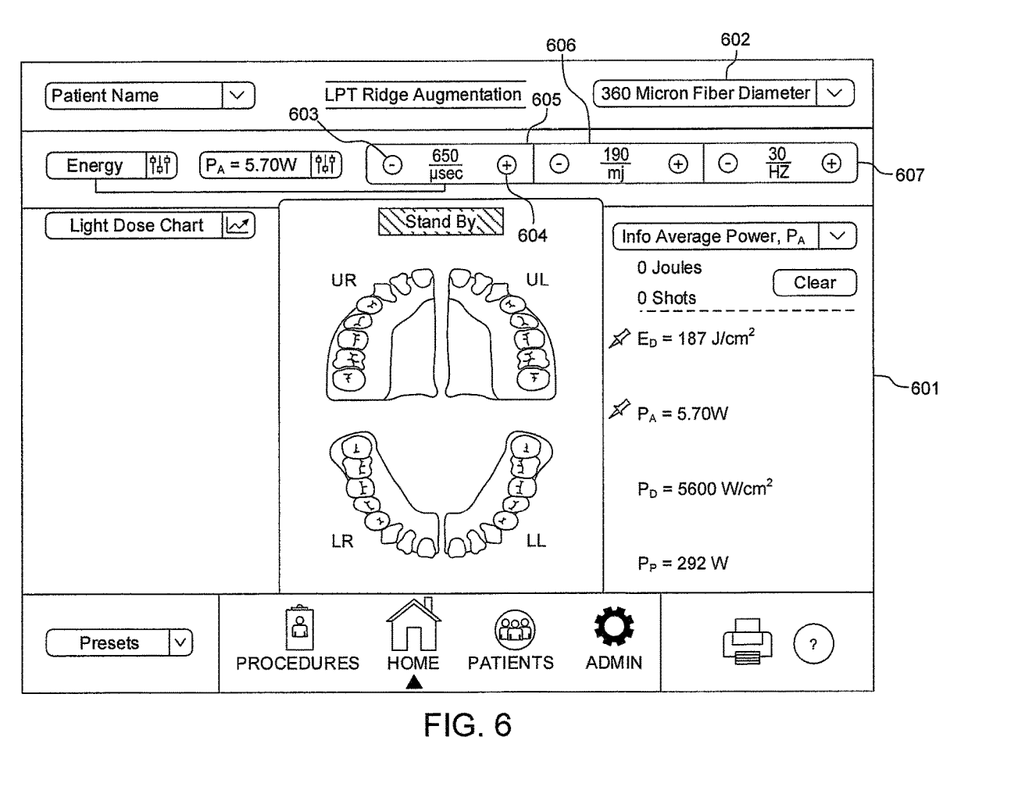
FIGS. 6 and 7 are views for explaining an electronic graphical user interface (eGUI) according to example embodiments.
Figure 7:
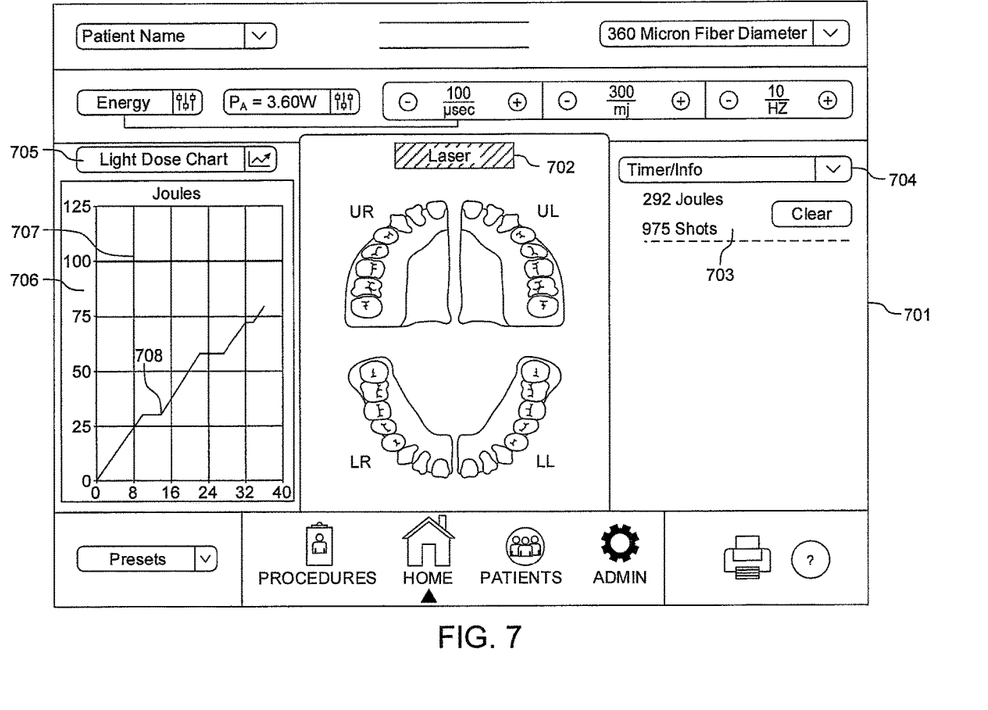

FIGS. 6 and 7 are views for explaining an electronic graphical user interface (eGUI) according to example embodiments.

FIG. 6 is a view for explaining a preset procedure overwrite, which allows the user to overwrite the therapeutic parameters of Preset Procedures listed on the Preset Procedures Screen. To enable this feature, the user must select a Preset Procedure from the Preset Procedures Screen. The Preset Procedures screen can be accessed by a right swipe from the home screen. A user may select a preset procedure by, e.g., clicking or tapping on it, and be automatically brought back to the home screen after the desired preset procedure has been selected.

As shown in FIG. 6, a control surface 601 for the home screen in the preset procedure overwrite depicts icons showing the therapeutic parameters or the energy settings: pulse duration in µsec 605, instantaneous energy in mJ 606, and pulse repetition rate in Hz 607 of the Preset Procedure, which can then be manipulated by using the (−) and (+) symbols (e.g., 603 and 604) next to each parameter. In addition, fiber diameter icon bar 602, located at the upper right side of the home screen, is selectable so that a drop-down list of selectable fiber diameters in microns will appear.

FIG. 7 depicts a control surface 701 with a light dose graph that changes as the laser is fired. In that regard, FIG. 7 shows a state in which the laser is currently being fired. Icon 702 indicates that the laser is currently being fired. To do so, the user might toggle STANDBY to READY, depress footswitch 314, and fire the laser, and then observe the yellow laser warning light.

The light dose chart 706 shows the amount of laser dosimetry applied so far during this active laser session (e.g., during an instance of pressing the footswitch), using a line 708, in Joules/time(s). At the same time, a line 707 shows the maximum allowable total joules which can safely or effectively be applied. This maximum allowable amount may change in dependence on, e.g., the procedure being performed. In that regard, additional lines may be displayed to show, for example, the maximum for particular phases of a multi-phase procedure, e.g., LANAP™ Ablation or LANAP™ Hemostasis or LARiP™ protocols.

The accumulation of Joules 703 on the light dose graph is also displayed on the right side of the home screen under the Timer/Info icon bar 704. The user may opt out of the light dose tracking by selecting the Light Dose Chart icon 705 once more, after which the graph 706 will disappear from the home screen.

FIG. 8 is a view for illustrating a Treatment Preset Control Surface Procedure Screen 801. In particular, example procedure settings are shown according to the fiber diameter and the therapeutic parameter settings. The Preset Procedures screen 801 has a list of patient treatment procedures that have the default therapeutic parameter settings according to the fiber diameter that the clinician has selected. In one example aspect, an image or icon (not shown) may be used to indicate that a video or photo tutorial is available for assistance on the corresponding procedure. In that regard, LARiP™ is not shown in the example of FIG. 8, but is likewise selectable from the pre-programmed procedures.

Other Embodiments

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read-only memory (ROM), random-access memory (RAM), erasable programmable read-only memory (EPROM), electronically erasable programmable read-only memory (EEPROM), dynamic random-access memory (DRAM), video RAM (VRAM), a magnetic tape or card, optical card, nanosystem, molecular memory integrated circuit, redundant array of independent disks (RAID), a non-volatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A laser-assisted ridge preservation method, using a laser device comprising:

first photothermally denaturing and vaporizing encapsulated granulomatous tissues with a free-running pulsed neodymium yttrium aluminum garnet laser device on a plurality of sides of a socket of an extracted tooth, wherein the free-running pulsed neodymium yttrium aluminum garnet laser device operates between 2.4 to 3.0 Watts average power, wherein the free-running pulsed neodymium yttrium aluminum garnet laser device has a pulse rate of 20 Hz, wherein the free-running pulsed neodymium yttrium aluminum garnet laser device has a pulse duration of 100 to 150 µsec, wherein a socket with blood remains after a tooth extraction;

second irradiating the socket and blood with the free-running pulsed neodymium yttrium aluminum garnet laser to form a stable thrombus, wherein the irradiating is performed with a repetition rate from the free-running pulsed neodymium yttrium aluminum garnet laser between 3.0 to 3.6 Watts average power, wherein the free-running pulsed neodymium yttrium aluminum garnet laser device has a pulse rate of 10 to 30 Hz, wherein the free-running pulsed neodymium yttrium aluminum garnet laser device has a pulse duration of 550 to 650 μsec;

third placing a bone graft material into the stable thrombus; and fourth performing photobiomodulation to accelerate wound healing wherein the photobiomodulation uses the free-running pulsed neodymium yttrium aluminum garnet laser with pulse duration of 100 μsec wherein the free-running pulsed neodymium yttrium aluminum garnet laser device operates between 1500 to 3000 Watts peak power.

2. The laser-assisted ridge preservation method of claim 1, wherein the tooth is extracted atraumatically along a root surface and through a periodontal ligament.

3. The laser-assisted ridge preservation method of claim 1, wherein the irradiating to achieve the stable thrombus is performed with an output energy from the free-running pulsed neodymium yttrium aluminum garnet laser between 100 to 200 Joules for a bicuspid tooth, wherein the irradiating is performed with an output energy from the free-running pulsed neodymium yttrium aluminum garnet laser between 300 to 600 Joules for a molar tooth.

4. The laser-assisted ridge preservation method of claim 1, wherein the bone graft material is a bone substitute which has a slow resorption by host tissues.

5. The laser-assisted ridge preservation method of claim 1, wherein the bone graft material is placed into the stable thrombus in an alveolus from the depth of the alveolar process to a crestal bone such that a graft is submerged and is contained within the stable thrombus.

6. The laser-assisted ridge preservation method of claim 1, wherein the photobiomodulation is used to accelerate wound healing after placement of the bone graft material.

7. The laser-assisted ridge preservation method of claim 1, wherein after the bone graft material is placed, the bone graft material is condensed.

8. The laser-assisted ridge preservation method of claim 1, wherein photobiomodulation with the free-running pulsed neodymium yttrium aluminum garnet laser is used to accelerate wound healing after placement, submergence, and condensation of a spongious bone graft material within the stable thrombus.

* * * * *